United States Patent
Domroese

(10) Patent No.: US 6,971,143 B2
(45) Date of Patent: Dec. 6, 2005

(54) MAGNETIC DETENT FOR ROTATABLE KNOB

(75) Inventor: Michael K. Domroese, Woodbury, MN (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 236 days.

(21) Appl. No.: 10/627,803

(22) Filed: Jul. 28, 2003

(65) Prior Publication Data

US 2004/0037707 A1 Feb. 26, 2004

Related U.S. Application Data

(62) Division of application No. 10/077,769, filed on Feb. 20, 2002, now Pat. No. 6,607,363.

(51) Int. Cl.[7] .............................................. E05B 1/00
(52) U.S. Cl. ..................................................... 16/441
(58) Field of Search ........................ 16/441, 903, 110.1, 16/111.1; 74/553; 200/336, 316, 345; 335/272–273, 335/296, 302–303; 340/815.64; 362/383, 362/398, 399; 417/63, 477.3, 477.8, 802

(56) References Cited

U.S. PATENT DOCUMENTS

| | | | |
|---|---|---|---|
| 3,344,378 A | * | 9/1967 | Wilhelmson ................ 335/272 |
| 3,411,155 A | * | 11/1968 | Watkins ................. 340/815.64 |
| 3,838,684 A | | 10/1974 | Manuel et al. |
| 3,855,560 A | * | 12/1974 | Ward .......................... 335/302 |
| 3,934,216 A | * | 1/1976 | Ward .......................... 335/272 |
| 4,256,437 A | | 3/1981 | Brown |
| 4,568,255 A | | 2/1986 | Lavender et al. |
| 4,726,588 A | * | 2/1988 | Caprio ................... 273/153 R |
| 5,394,739 A | | 3/1995 | Garvey, III et al. |
| 5,586,872 A | | 12/1996 | Skobelev et al. |
| 5,657,000 A | | 8/1997 | Ellingboe |
| 5,862,715 A | * | 1/1999 | Lemire ........................ 74/553 |
| 5,954,192 A | * | 9/1999 | Iitsuka ....................... 200/336 |
| 5,965,855 A | | 10/1999 | Tanazawa et al. |
| 6,424,245 B1 | * | 7/2002 | Rector et al. ................ 335/220 |
| 6,812,816 B1 | * | 11/2004 | Easton ......................... 335/205 |

FOREIGN PATENT DOCUMENTS

| | | | | | |
|---|---|---|---|---|---|
| GB | 2067655 A | * | 7/1981 | ........... | E05D 11/10 |
| GB | 2072625 A | * | 10/1981 | ........... | G01F 11/32 |

* cited by examiner

*Primary Examiner*—Chuck Y. Mah
(74) *Attorney, Agent, or Firm*—Mark L. Mollon; MacMillian, Sobanski & Todd

(57) ABSTRACT

A roller pump including a stator and a rotor assembly disposed within the stator. The rotor assembly includes a rotor hub, a first roller slide and a second roller slide slidingly disposed within the rotor hub. Each of the roller slides rotatably supports a roller. An occlusion adjustment knob for adjusting a radial position of the first and second roller slides and a magnetic detent assembly for providing an audible indicator as the occlusion adjustment knob is rotated.

10 Claims, 5 Drawing Sheets

MAGNETIC DETENT FOR ROTATABLE KNOB

This application is a divisional of application Ser. No. 10/077,769, filed on Feb. 20, 2002, now U.S. Pat. No. 6,607,363.

TECHNICAL FIELD

The present invention is directed to a detent assembly for a rotatable knob, and more particularly, to a magnetic detent assembly for providing audible feedback during the rotation of an occlusion adjustment knob on a peristaltic pump.

BACKGROUND OF THE INVENTION

Peristaltic pumps are commonly utilized in medical applications. For instance, such pumps are often employed during cardiovascular surgery to facilitate circulation of blood between a patient and a heart-lung machine. Other common medical uses are the transfer of blood between a patient and a kidney dialyzer, and intravenous feeding of IV solutions. Generally, peristaltic pumps are simply structured, generate a constant flow, and employ disposable tubes as a member for fluid transfer.

Peristaltic pumps are relatively simple in construction and typically include a housing having rollers which progressively compress a flexible tube at spaced intervals against an arcuate surface or raceway so as to flatten or locally reduce the cross-sectional area of the tube. In this manner, fluid leading to the flexible tube is continuously forced through the flexible tube by one or another of the rollers as it proceeds along the flexible tube over the arcuate surface or raceway.

A conventional roller pump 10, as shown in FIG. 1, comprises a drive mechanism 14 furnished with a drive shaft 12, a rotating shaft 16 which rotates according to the rotation of drive shaft 12, and a hollow pump head 20 fixed to a housing 18 to which drive mechanism 14 is attached. This pump head 20 integrally incorporates a bearing block 24 through which rotating shaft 16 is inserted and rotatably supported by a pair of bearings 22 and a stator 26 arranged on the upper portion of bearing block 24. On the upper surface of stator 26 is formed a recess 28 through which the upper end of rotating shaft 16 is protruded. While this recess 28 is radially and outwardly spaced at a certain distance from the outer circumferential surface of rotating shaft 16, its inner circumferential surface 28a is coaxial with rotating shaft 16.

A rotor assembly 30 is attached to the upper portion of rotating shaft 16 in such a way as to be placed inside recess 28 of stator 26 and to stay opposite the inner circumferential surface 28a thereof. This rotor 30 is fixed to rotating shaft 16 through a bolt 32, and is so constructed as to integrally rotate along with rotating shaft 16. On the outer circumferential surface of rotor 30, at least one roller 34 is arranged so as to rotate about its own axes. A tube 36 which is filled with blood or other fluid material is placed between rotor 30 and stator 26. Tube 36 is clamped between respective rollers 34, which are attached to rotor 30, and inner circumferential surface 28a of stator 26, thereby maintaining tube 36 in a closed state at the point at which it is clamped.

Thus, in a conventional roller pump 10, rotor 30 is rotated by the rotational motion of rotating shaft 16 driven by drive mechanism 14, and the clamped portions of tube 36 move according to the revolution of rollers 34 around rotating shaft 16. Therefore, fluid inside tube 36 is transferred according to the revolution of rollers 34. The rate of rotation of the rotating shaft 16 and hence the rollers 34 is normally adjustable so that the pumping rate of the fluid within tube 36 can be adjusted. However, the pumping rate can also be adjusted by adjusting the degree to which the rollers compress the flexible tube. This can be done in peristaltic pump assemblies by providing an adjustment mechanism for adjusting the distance between the axes of the rollers and hence the distance between the roller surface and the inner circumferential surface 28a of stator 26. Another important reason for peristaltic pumps to be adjustable in this fashion is that the compressibility, size, and other qualities of the flexible tube can vary considerably.

A rotor assembly 30' having an adjustable occlusion capability, as shown in FIG. 2, comprises a rotor hub 40, and opposing roller slides 42, each of which carries at least one roller 34 on the outer circumferential surface thereof. The roller slides 42 are extended or retracted from the hub 40 by turning the knob 44 on the top of the rotor hub. The extension or retraction of the roller slides thereby changes the occlusion of the flexible tube within the peristaltic pump. The knob 44 is usually provided with a detent assembly or some other type of mechanism which provides an audible feedback or signal as the knob is being rotated.

Typical detent assemblies disposed in the occlusion adjustment knob 44 include spring loaded balls or plungers that ride against a plate or disk with a series of slots or shallow holes. This type of detent mechanism provides both tactile and audible feedback as the plate moves over the spring loaded ball or plunger. However, both the tactile and audible feedback can be significantly reduced to the point of being nearly undetectable if there is significant resistance to the movement of the plate or disk. For instance, when there is a significant resistance to the rotation of the adjustment knob, such as caused by increased compression of the flexible tube, for instance, the feel and sound of a spring loaded detent may be almost undetectable.

In addition, the metal-to-metal contact between the plate and the spring loaded ball or plunger tends to create wear which in turn may affect the precise positioning required by the spring loaded ball within the slots or shallow holes of the plate. More particularly, the corners of the notches or holes in a spring loaded detent plate or disk will tend to become rounded, changing the feel and sound of the detent as the plate wears under contact. Commercially available spring loaded ball plungers often have a 0.025 inch or less range of travel. The sound and feel of a spring loaded detent can also be quite sensitive to the force of the spring on the ball. Because of the sensitivity and limited range of travel, the use of a spring loaded ball can require that the tolerances on the mechanical assembly be rather tight in order to assure that the ball rides properly and consistently on the moving plate or disk.

Accordingly, there is a need in the art for a reliable detent assembly for providing an audible indication of rotation of a knob, which is not compromised when resistance to movement is encountered and which does not require the precise positioning of the prior art.

SUMMARY OF THE INVENTION

A preferred embodiment of the present invention overcomes these drawbacks of the prior art by providing a roller pump comprising a stator, a rotor assembly disposed within the stator, the rotor assembly including a rotor hub, a first roller slide and a second roller slide slidingly disposed within the rotor hub, and each of the roller slides supporting a roller. An occlusion adjustment knob is provided for adjusting a radial position of the first and second roller slides and a magnetic detent assembly provides an audible indicator as the occlusion adjustment knob is rotated. A further preferred embodiment of the roller pump comprises a detent ring, with the magnetic detent assembly being disposed proximate to the detent ring. In a preferred embodiment, the magnetic detent assembly includes a base member having two sealed enclosures, each of the enclosures including a magnetically attractable member and a magnet. Preferably, the magnetically attractable member is a sphere, such as a steel ball.

A further preferred embodiment of the present invention is directed to a knob assembly comprising a rotatable knob having an under surface and a top surface for gripping by a user, a notched plate rotatable with the rotatable knob and arranged proximate to the under surface of the rotatable knob, and a magnetic detent assembly disposed substantially stationary proximate to the notched plate. Rotation of the rotatable knob and the notched plate over the magnetic detent assembly thus provides a user with an audible indicator of rotation.

A still further preferred embodiment of the present invention provides a magnetic detent assembly comprising a base member having a top surface and a bottom surface, at least one magnetically attractable member disposed in a recess in the base member, and at least one magnet disposed in the base member. The at least one magnetically attractable member is movably contained in the recess between the top surface of the base member and the at least one magnet.

BRIEF DESCRIPTION OF THE FIGURES

These, and other, objects, features and advantages of the present invention will become more readily apparent to those skilled in the art upon reading the following detailed description, in conjunction with the appended drawings, in which.

DETAILED DESCRIPTION OF THE INVENTION

Figure 1:
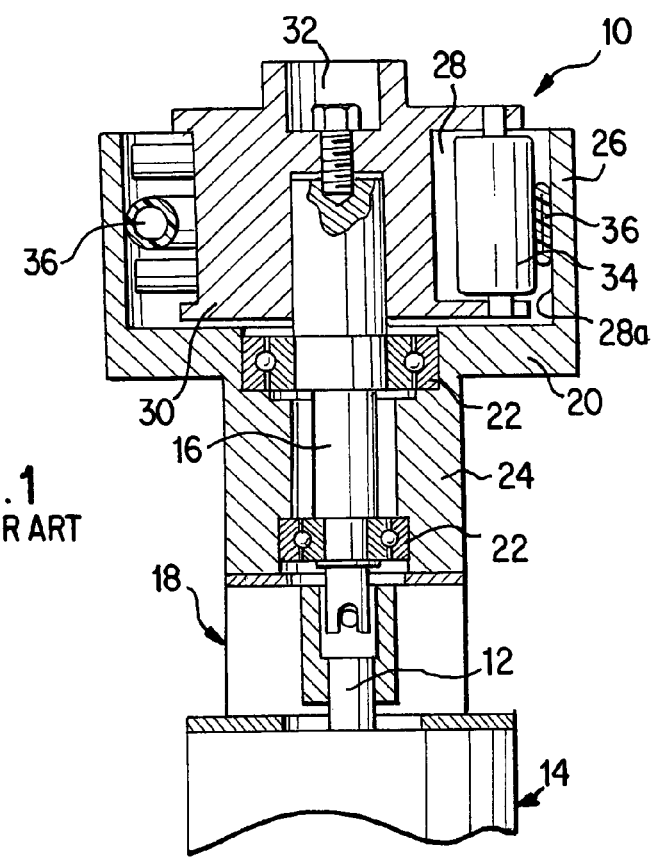
FIG. 1 is a cross-sectional view of a peristaltic pump as known in the prior art.
Figure 2:
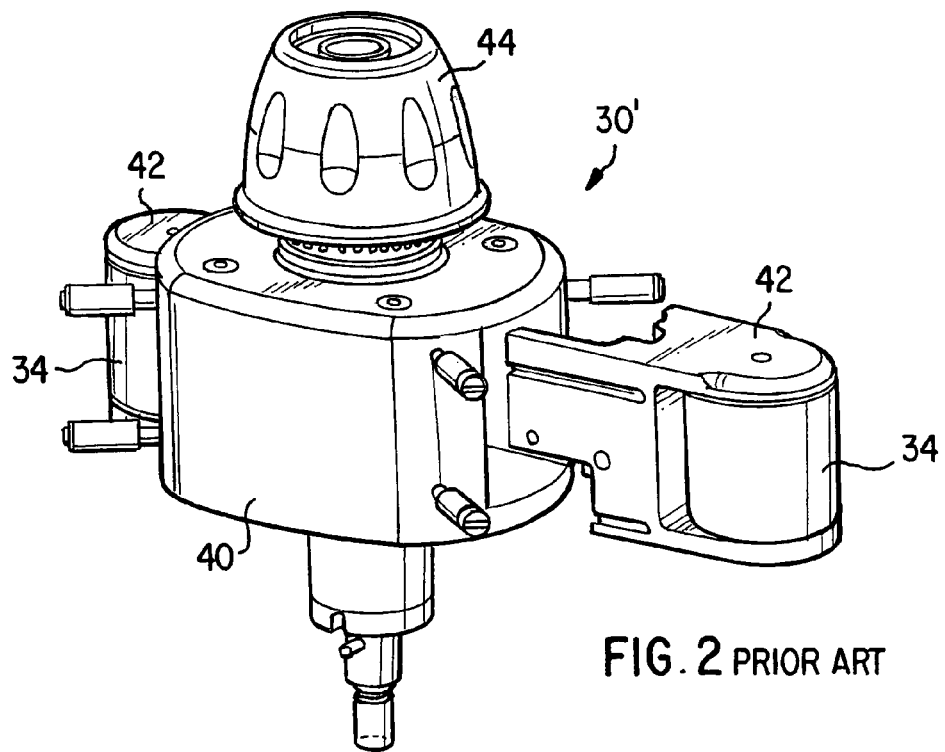
FIG. 2 is a perspective view of an alternative rotor assembly for a peristaltic pump as known in the art.
Figure 3:
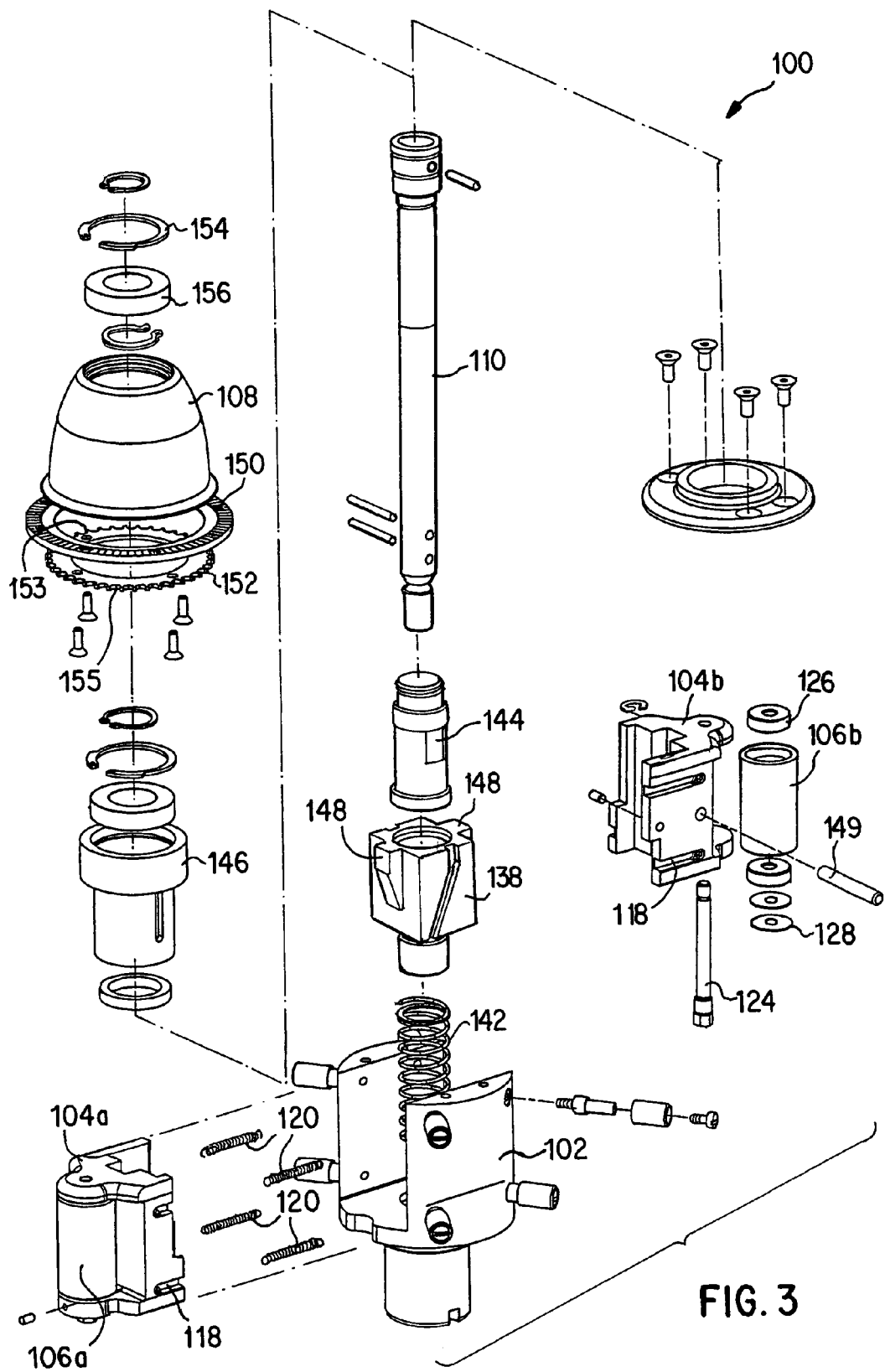
FIG. 3 is an exploded view of a rotor assembly for a peristaltic pump according to the present invention.

A peristaltic pump rotor assembly according to the present invention is shown generally by reference numeral 100 in the exploded view of FIG. 3. Rotor assembly 100 includes a pump or rotor hub 102, at least one and preferably two opposing roller slides 104a, 104b, a roller 106a, 106b disposed within each roller slide, respectively, and an adjustment knob 108 for adjusting the occlusion of the flexible tube within the pump. The rotor assembly 100 is rotatably supported within a stator similar to that shown in FIG. 1 and as known in the art, and the inner circumferential surface of the stator forms the raceway for the rollers 106a, 106b of the present invention. A main shaft 110 extending through the rotor assembly 100 rotates according to the rotation of a drive shaft, which is rotated by a conventional drive mechanism, as shown in FIG. 1, for example.

Each of the roller slides 104a, 104b includes a plurality of recesses or channels 118 for receiving an extension spring 120. Each of the channels 118 includes, preferably at an outer end thereof, a peg to which the opposing ends of the springs are attached. As such, the opposing roller slides 104a and 104b are interconnected by a plurality of springs 120. The rollers 106a, 106b are firmly held in the proper position within the roller slides 104a, 104b, respectively, by a roller shaft 124. Various bearings 126 and washers 128 may also be used for mounting the rollers 106a, 106b within the roller slides 104a, 104b, respectively.

As shown in the illustrated embodiment, the rotor assembly 100 further includes a cam block 138 which is spring loaded by a spring 142. A guide collar 144 engages an upper surface of the cam block 138 and vertically adjusts the position of cam block 138 through rotation of the adjustment knob 108 and a screw adjustment member 146 which moves downward and thereby correspondingly moves the guide collar 144 in a downward direction. The cam block 138 includes opposing wedge-shaped projections 148 which engage a corresponding dowel pin 149 on an inner surface of each roller slide 104a, 104b. Thus, as the adjustment knob 108 is rotated clockwise, for example, and screw adjustment member 146 correspondingly moves downward so as to move guide collar 144 in a downward direction, cam block 138 is also moved downward such that the wedge projections 148 on the cam block 138 force the roller slides 104a, 104b radially outward against the force of extension springs 120.

The adjustment knob 108 also includes an occlusion indicator ring 150 and a detent ring 152 for providing an audible indication of the degree of rotation of the knob 108. As shown, the detent ring 152 preferably has a scalloped periphery defining a plurality of teeth 153 with generally U-shaped cut-outs 155 therebetween. A plurality of retaining rings 154 and bearings 156 may also be provided.

Figure 4:
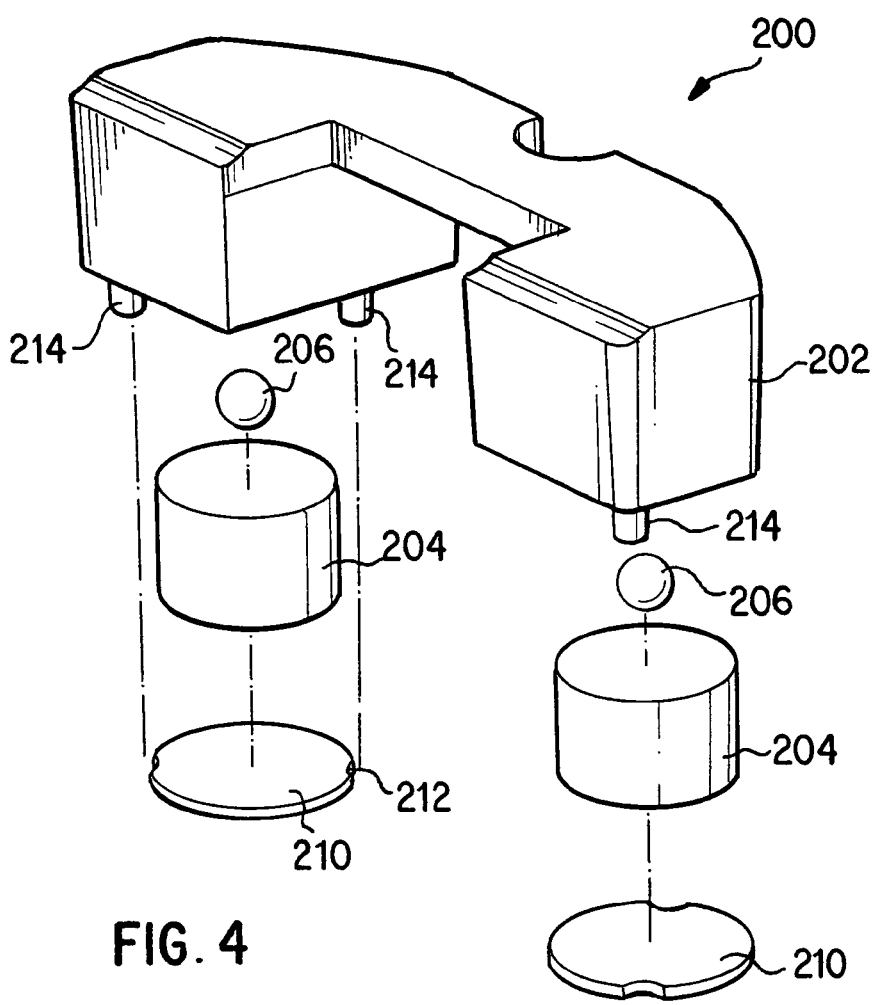
FIG. 4 is an exploded view of a magnetic detent assembly according to the present invention.
Figure 5:
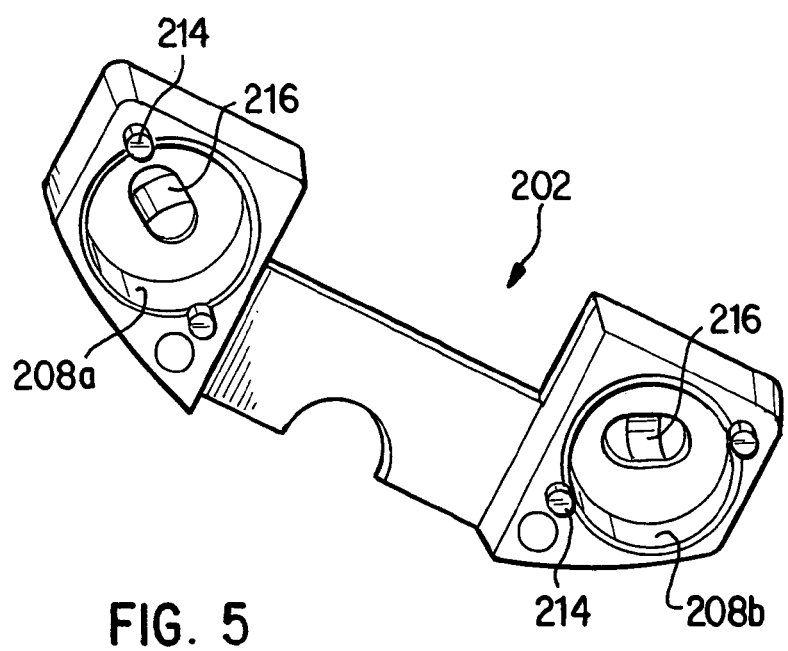
FIG. 5 is a bottom perspective view of a base thereof.
Figure 6A:
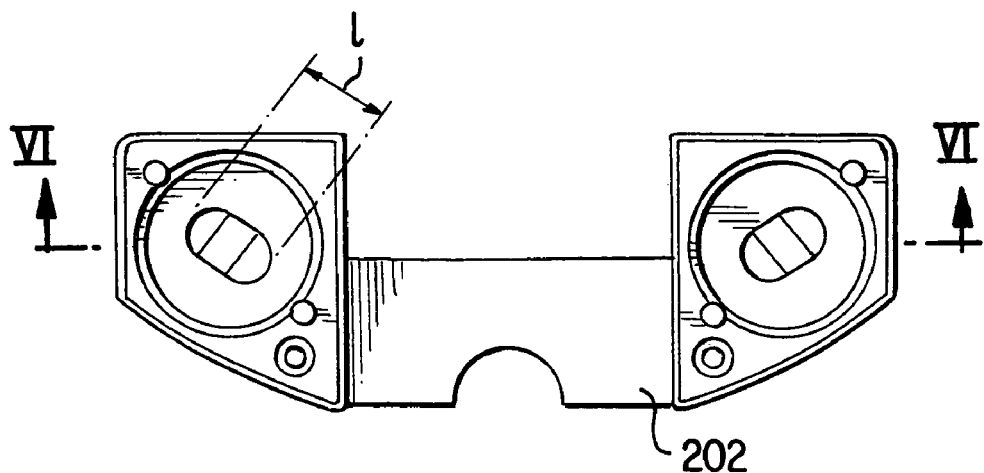
FIG. 6A is a bottom plan view of a base thereof.
Figure 6B:
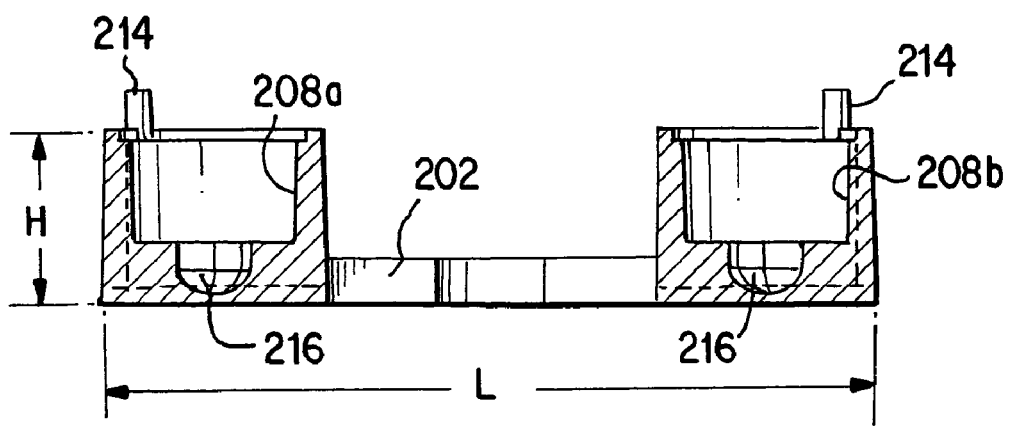
FIG. 6B is a cross-sectional view taken along line VI—VI in FIG. 6A.
Figure 6C:
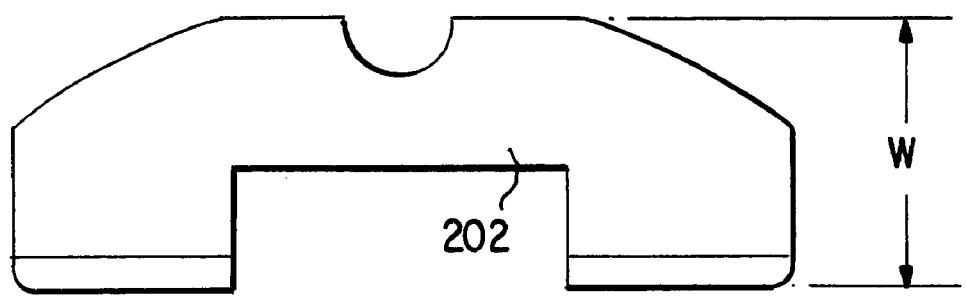
FIG. 6C is a top plan view of a base thereof.

Whereas the prior art included spring loaded balls or plungers that interacted with the cut-outs 155 in detent ring 152, the present invention provides a magnetic detent assembly, as shown by reference numeral 200 in the exploded view of FIG. 4. The magnetic detent assembly produces audible clicks as the notched plate or detent ring 152, such as associated with adjustment knob 108 of the peristaltic pump, is passed over the detent assembly 200. The notched detent plate 152 must be made of a material that is attracted to a permanent magnet. The detent assembly 200 includes a base 202, at least one permanent magnet 204, and at least one ball 206, preferably made from steel or other magnetically attracted material. The base 202 is preferably made from a material that is not attracted to the permanent magnet.

Referring also to FIGS. 5 and 6A–6C, a preferred embodiment of the magnetic detent assembly 200 is more clearly illustrated. The base 202 has a generally U-shaped configuration defined by a center portion and two extending legs, with recesses 208a, 208b disposed in each respective leg. In a bottom surface of each recess 208a, 208b is formed a ball receiving recess 216. A ball 206 is disposed in each of the recesses 216 within recesses 208a, 208b, and then a permanent magnet 204 is placed thereover. A lid 210 is then disposed over each of the magnets to seal the magnet and ball within each recess in the base 202. Ultrasonic welding may, for example, be used to seal the lid to the base. In a preferred embodiment, the ball receiving recesses 216 have a longitudinal length/of approximately 0.2 inches and a steel ball having a diameter of approximately 3 mm is disposed therein. Thus, the ball will move from one side of the recess to the other side of the recess as the notched plate passes thereover, as explained in greater detail below. The ball recesses 208a, 208b have a depth of approximately 0.122 inches +/−0.002 tolerance. The overall length L of the detent assembly is approximately 1.816 inches and the overall width W thereof is approximately 0.641 inches, while the height H of the detent assembly is approximately 0.410 inches. As should be apparent to one skilled in the art, these specific dimensions are merely exemplary, and other sizes and shapes could, of course, also be used within the scope of the present invention to obtain the desired audible indication signal.

The lid 210 preferably has a notch 212 for receiving a post 214 formed on the base 202. It is this post 214 which is melted during the use of ultrasonic welding to thereby hold the lid to the base.

Figure 7A:
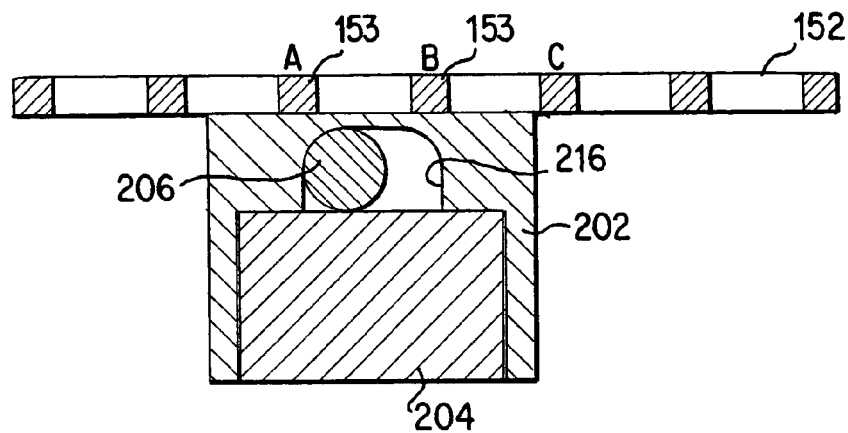
FIGS. 7A–7C illustrate the operation of the magnetic detent assembly of the present invention.
Figure 7B:
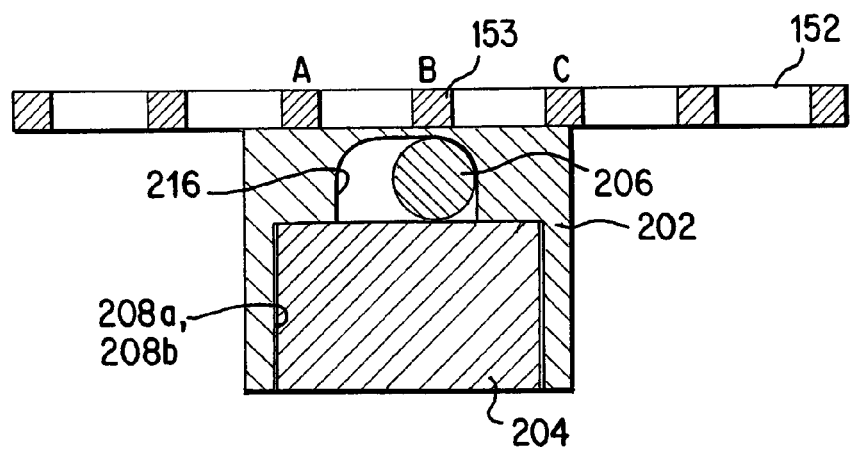
Figure 7C:
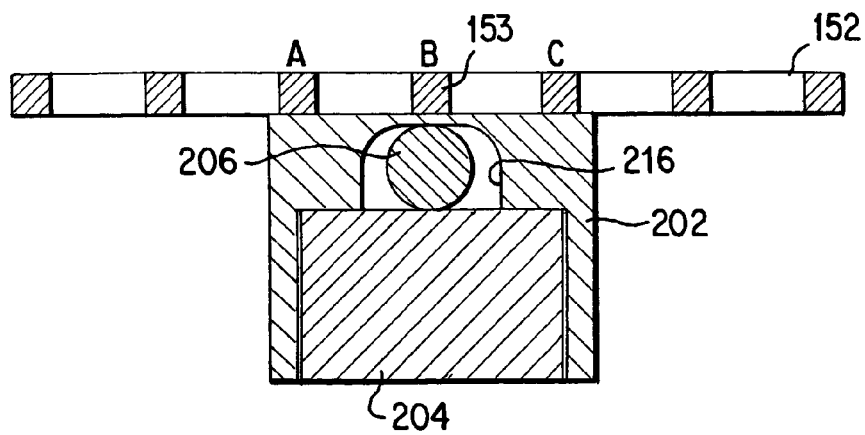

The operation of the detent assembly 200 can be described as follows with reference to the schematic illustrations of FIGS. 7A–7C. As the knob 108 is rotated, and notched plate 152 rotates therewith, the steel ball 206 is pulled toward the nearest tooth 153 in the notched plate 152 (i.e., tooth A). The magnetic permeability of a material such as steel is far greater than that of air, therefore the magnetic flux of the permanent magnet will travel primarily through the nearest tooth of the notched plate, and the force induced by this field will tend to pull the steel ball 206 between the magnet 204 and the tooth 153. As the notched plate 152 moves to the left over the substantially stationary magnetic detent assembly 200, as the rotatable knob 108 is turned, at some point more magnetic flux will travel through the next tooth 153 to the right (i.e., tooth B) and the steel ball 206 will be pulled to the right side of the recess 216 in the base 202. The ball 206 will be pulled quickly to the other side of the recess 216 and in so doing will make a clicking noise as the ball 206 hits the side of the recess 216. As the notched plate 152 continues to travel to the left, the ball follows the tooth from the right to the left side of the recess 216 in the base 202. The sequence of operation described above repeats with the ball making another clicking noise as it moves from tooth B to tooth C. If the direction of the plate travel were reversed such that the plate moved to the right, the operation of the detent would mirror that described above. In this case, the ball would make clicking noises as it hits the left rather than the right side of the recess.

As an advantage of the magnetic detent assembly of the present invention, the clicks produced by the magnetic detent are much less sensitive to resistance to the movement of the notched plate than a spring loaded detent. Whereas the feel and sound of a spring loaded detent may be almost undetectable when there is significant resistance to the rotation of the adjustment knob, the sound of the magnetic detent of the present invention remains substantially the same regardless of the level of resistance to the knob rotation. Moreover, the magnet and the ball can be sealed in the base and are therefore less susceptible to dirt and corrosion than a spring loaded detent. Similarly, minimal and perhaps no wear occurs as the notched plate moves over the detent assembly because there is no metal to metal point contact.

A magnetic detent assembly 200 has been implemented in connection with the rotation of the adjustment knob 108 on the rotor assembly of a peristaltic pump. As the adjustment knob 108 is rotated, the span of the rollers is adjusted, thereby changing the occlusion of the tube in the pump. The magnetic detent assembly 200 is designed to float in the vertical direction on the pump tongue. The detent assembly is magnetically held to the bottom surface of the adjustment knob 108 and the notched plate 152 moves directly over the detent assembly. Therefore, the function and sound of the magnetic detent is not sensitive to the tolerances between the various parts on which the notched plate and the base of the detent assembly are mounted, as the base will magnetically ride on the notched plate. In addition, it has been found that the sound of the detent is consistent regardless of the degree of tube occlusion and the resistance to the rotation of the adjustment knob. The magnetic detent assembly preferably includes two detents, that is, first and second steel balls 206, one in the bottom recess 216 of each of the recesses 208a, 208b, which are disposed on each side of the pump tongue. The two detents are preferably used to increase the resolution of the detent, and the number of clicks per revolution of the knob thus increases by a factor of two. It is also possible to further increase the number of clicks per revolution by including additional detents in the design.

While the above described magnetic detent assembly has been illustrated with respect to a preferred embodiment and use within an occlusion adjustment knob for a peristaltic pump, it should be apparent to one skilled in the art that the applications of the detent assembly extend further to other devices and situations within the scope of the present invention.

What is claimed is:

1. A knob assembly comprising:
    a rotatable knob having an under surface and a top surface;
    a notched plate rotatable with said rotatable knob and arranged proximate to said under surface of said rotatable knob;
    a magnetic detent assembly disposed substantially stationary proximate to said notched plate, wherein said magnet detent assembly includes a base member having at least one sealed enclosure, said at least one enclosure including a magnetically attractable member and a magnet;
    wherein rotation of said rotatable knob and said notched plate over said magnetic detent assembly provides a user with an audible indicator of rotation.

2. The knob assembly of claim 1 wherein said magnetically attractable member is a sphere.

3. The knob assembly of claim 2 wherein said sphere is a steel ball.

4. The knob assembly of claim 1 wherein said base member includes a first recess for receiving said magnet.

5. The knob assembly of claim 4 wherein said first recess includes a second recess therein, said second recess dimensioned for receiving said magnetically attractable member.

6. The knob assembly of claim 1 wherein said magnetic detent assembly has a central area and a leg extending from each end thereof, thereby defining a generally U-shaped configuration.

7. A magnetic detent assembly for generating audible feedback during relative movement past a magnetizable structure, comprising:
    a base member having a top surface and a bottom surface;
    at least one magnetically attractable member disposed in a recess in said base member, said recess being elongated between a pair of opposite sides formed within said base member; and
    at least one magnet disposed in said base member between said recess and said botton surface;
    wherein said at least one magnetically attractable member is movably contained in said recess between said top surface of said base member and said at least one magnet, and wherein said at least one magnetically attractable member strikes at least one of said opposite sides during movement of said magnetizable structure past said top surface to generate said audible feedback.

8. The magnetic detent assembly of claim 7 wherein said recess is formed in a bottom surface of a magnet receiving recess in said base member.

9. The magnetic detent assembly of claim 7 wherein said at least one magnetically attractable member comprises a sphere.

10. The magnetic detent assembly of claim 7 where said at least one magnetically attractable member is formed from steel and said base member is formed from a plastic material.

* * * * *